United States Patent [19]

Schiffers et al.

[11] Patent Number: 4,663,931

[45] Date of Patent: May 12, 1987

[54] POWER GENERATING STATION WITH AN INTEGRATED COAL GASIFICATION PLANT

[75] Inventors: Ulrich Schiffers, Eckental; Rainer Müller, Erlangen, both of Fed. Rep. of Germany

[73] Assignee: Kraftwerk Union Aktiengesellschaft, Mülheim, Fed. Rep. of Germany

[21] Appl. No.: 855,751

[22] Filed: Apr. 24, 1986

Related U.S. Application Data

[62] Division of Ser. No. 614,325, May 25, 1984.

[30] Foreign Application Priority Data

Jun. 3, 1983 [DE] Fed. Rep. of Germany ....... 3320227

[51] Int. Cl.$^4$ ................................................ F02C 3/28
[52] U.S. Cl. ..................................... 60/39.07; 60/39.12
[58] Field of Search ............... 60/39.07, 39.12, 39.182, 60/39.465; 518/702, 703

[56] References Cited

U.S. PATENT DOCUMENTS

| | | | |
|---|---|---|---|
| 3,849,662 | 11/1974 | Blaskowski et al. | 60/39.182 |
| 3,868,817 | 3/1975 | Marion et al. | 60/39.12 |
| 3,904,386 | 9/1975 | Graboski et al. | 518/703 |
| 4,005,996 | 2/1977 | Hausberger et al. | 518/703 |
| 4,019,314 | 4/1977 | Springmann | 60/39.12 |
| 4,404,414 | 9/1983 | Penick et al. | 585/408 |

FOREIGN PATENT DOCUMENTS

| | | |
|---|---|---|
| 38138 | 10/1981 | European Pat. Off. |
| 47596 | 3/1982 | European Pat. Off. |
| 2807326 | 8/1979 | Fed. Rep. of Germany |
| 3100751 | 1/1982 | Fed. Rep. of Germany |
| 1167493 | 10/1969 | United Kingdom |
| 2075124 | 11/1981 | United Kingdom |

OTHER PUBLICATIONS

Hamilton & Lehman, "Novel Gas Turbine Cycles with Coal Gasification", ASME Paper 79-WA/Ener-6; Dec. 1979.

Foster-Pegy, R. W., "The Integration of Gasification with Combined Cycle Power Plants", in *Combustion;* Dec. 1979.

*Primary Examiner*—Louis J. Casaregola
*Attorney, Agent, or Firm*—Herbert L. Lerner; Laurence A. Greenberg

[57] ABSTRACT

Power generating plant with an integrated coal gasification plant, with a heat exchanger and gas purification plant connected to the coal gasifier, with a gas turbine and steam power generating plant part connected to the heat exchanger and gas purification plant, and with a methanol synthesis plant. The methanol generated in the methanol synthesis plant as well as the synthesis exhaust gas of the methanol synthesis can be fed, at least partially, to a further subplant for a second chemical manufacturing process and the excess synthesis exhaust gas from the methanol synthesis and the exhaust from this further subplant, to the combustion chamber of the gas turbine power generating plant part.

9 Claims, 2 Drawing Figures

POWER GENERATING STATION WITH AN INTEGRATED COAL GASIFICATION PLANT

This is a division of application Ser. No. 614,325, filed May 25, 1984 (allowed).

BACKGROUND OF THE INVENTION

1. Field of the Invention

The invention relates to a power generating station with an integrated coal gasification plant, with a heat exchanger and gas purification plant connected to the coal gasifier, a gas turbine and a steam power generating station part connected to the heat exchanger and a gas purification plant, and a methanol synthesis plant.

2. Description of the Prior Art

British Patent 20 75 124 discloses a power generating plant in which a gas turbine is supplied with synthesis gas from a coal gasification plant. The gas turbine drives an electric generator. The waste heat of the gas turbine is utilized in this power generating plant for generating steam. A steam turbine and a further electric generator are driven with the steam. Part of the synthesis gas produced is fed to a methanol sythesis plant. The methanol produced is stored in this power generating plant and is burned in the gas turbine in addition to the synthesis gas for equalizing load peaks. This power generating plant at times of low load, generates methanol to an increased extent and the so-produced methanol can be sold as raw material unless it is needed for equalizing peak loads. Apart from the fact that only a small part of the produced methanol is available as a product of the plant due to frequent levelling out of peak loads, the production costs for the methanol are not substantially lower than those of corresponding production processes which are independent of a power generating station.

SUMMARY OF THE INVENTION

An object of the invention is to improve the efficiency of such a power generating station and to produce in the process chemical raw materials inexpensively.

With the foregoing and other objects in view, there is provided in accordance with the invention a power generating station with an integrated coal gasification plant comprising (a) a coal gasification plant which contains a gasifier for gasification of coal to produce raw fuel gas containing a mixture of gaseous constituents including CO, $H_2$, $CO_2$ and $H_2S$, an air separation unit to separate air into oxygen and nitrogen, and a compressor to supply the air separation unit with air, (b) a gas turbine power plant which includes a gas turbine, a combustion chamber of the gas turbine, an air compressor for introduction of air into the combustion chamber, and a generator coupled to the turbine, (c) a steam generating station which includes a steam generator, a high pressure and low pressure turbine, a feedwater tank to collect the condensate and a feedwater pump to feed water to the steam generator, (d) a heat exchanger in which the raw gas is utilized to generate steam and conduit means for passage of the generated steam to the steam turbine, and a gas purification plant for the removal of impurities to produce a purified gas, (e) a methanol synthesis plant having a methanol synthesis reactor for the partial conversion of the purified gas from the gasifier into methanol and a methanol separator connected to the synthesis reactor for the separation of the reaction products from the synthesis reactor into liquid methanol and methanol synthesis exhaust gas.

(f) an additional synthesis plant for the utilization of at least part of the methanol and the methanol synthesis exhaust gas to produce a product other than methanol and a residual gas as a byproduct, and connecting means for supplying excess methanol synthesis exhaust gas and residual gas to the combustion chamber.

Other features which are considered as characteristic for the invention are set forth in the appended claims.

Although the invention is illustrated and described herein as embodied in a power generating station with an integrated coal gasification plant, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings, in which.

DETAILED DESCRIPTION OF THE INVENTION

Figure 1:
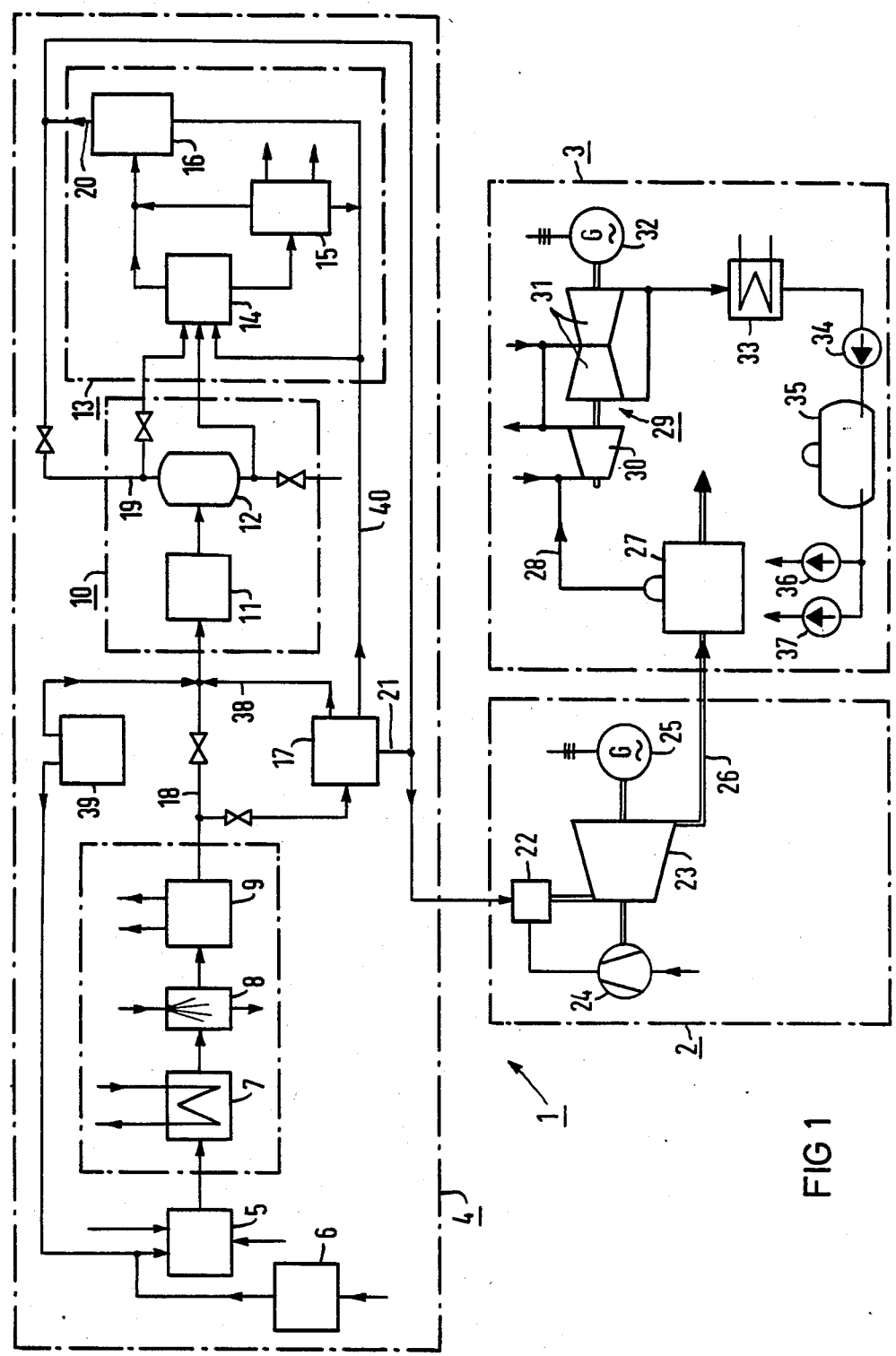
FIG. 1 shows a power generating station according to the invention with a connected plant for the manufacture of methanol and acetic acid.

In a power station of the type mentioned at the outset, the methanol of the methanol synthesis plant as well as the synthesus waste gas of the methanol synthesis are fed, according to the invention, at least partially to a further subplant for treatment in a second chemical production process. The excess synthesis waste gas from the methanol synthesis and the exhaust gas from this second partial plant are directed to the combustion chamber of the gas turbine power generating part. These two mutually coupled subplants, each for a chemical production process, are integrated into the power generating plant through the use of the synthesis gas produced for the production of methanol and by feeding a part of the methanol and the exhaust gas from the methanol synthesis to another chemical production process. This integration enables these chemical raw materials to be produced at least cost. Due to the combustion of the excess synthesis waste gases in the combustion chamber of the gas turbine, the expense for establishing stoichiometric conditions of the starting gases can be reduced, without thereby losing the energy content of the incompletely reacted synthesis waste gases.

In a particularly practical further embodiment of the invention, the methanol synthesis plant can be designed without recirculation, i.e. without a recirculation line and loop compressor. Thereby, the investment is reduced since such equipment is no longer necessary due to the integration. Also the energy required for the recirculation of the not fully reacted synthesis waste gases is reduced thereby.

In a particularly advantageous further embodiment of the invention, an acetic acid synthesis plant can be used as a further subplant. This has the advantage that the thermal energy content of the exhaust gases of the methanol synthesis is utilized for the production of acetic acid. In addition, the synthesis waste gases of the continuous-flow methanol synthesis which has a composition not of stoichiometric proportion is utilized for the following acetic acid synthesis.

The material yield can be improved if, in a particularly advantageous further embodiment of the invention, a gas separation plant is connected to the gas line leading to the methanol synthesis reactor, and part of the gas flowing to the methanol synthesis reactor is diverted and sent to the gas separation plant wherein a hydrogen-rich fraction and a carbon monoxide-rich fraction are separated. The hydrogen-rich fraction is admixed to the gas stream flowing into the methanol synthesis reactor and the fraction rich in carbon monoxide is fed to the acetic acid reactor as well as to the combustion chamber of the gas turbine power generating part. Thereby, the ratio of hydrogen to carbon monoxide in the synthesis gas sent to the methanol synthesis reactor is brought closer to the desired stoichiometric ratio. This increases the yield of methanol. At the same time, the carbon monoxide content of the gas fed to the acetic acid reactor can be increased, whereby a larger share of the produced methanol can be converted into acetic acid.

An even closer approximation of the desired stoichiometric ratio of $H_2$ to CO in the composition of th synthesis gas to the methanol synthesis reactor can be achieved by associating the methanol the methanol reactor with a water electrolyzing plant which converts water into oxygen and hydrogen. Oxygen from the water electrolizing plant is connected to the coal gasifier and a hydrogen line is connected to the gas line leading to the methanol synthesis reactor. Thereby, the material yield of methanol can be improved considerably and at the same time, the air separation plant preceding the coal gasifier is relieved of part of its load of separating air into oxygen and nitrogen.

In an alternative, particularly advantageous embodiment of the invention, a plant for producing vinyl acetate can be used as a further subplant. Here also, the not completely reacted synthesis exhaust gases of the preceding methanol synthesis which is operated with purified gas of not stoichiometric composition can be utilized. The manufacture of vinyl acetate following the methanol continuous flow synthesis is particularly practical because these exhaust gases of the continuous flow methanol synthesis have approximately the composition which is needed for the synthesis of vinyl acetate. Thereby, the gas separation plant which must otherwise be provided in the manufacture of acetic acid can be eliminated. Again, building blocks, which would be necessary otherwise for the synthesis of vinyl acetate, are obtained from the synthesis exhaust gases. Thereby, a further valuable chemical raw material, namely synthesis exhaust gases, which may be salable in the market at a profit can be produced in this manner at low cost. The production of chemical raw materials produced here also contribute to the ability of operating the coal gasifier at full load even though the gas turbine load is low.

Further details of the invention will be explained with the aid of two embodiment examples shown in the drawings.

FIG. 1 shows schematically a power generating station 1 which consists of a gas turbine power plant part 2, a steam power generating station part 3 and a plant 4 for the production of chemical raw materials. The plant 4 for the manufacture of chemical raw materials contains a coal gasifier 5 with an associated air separation plant 6, a heat exchanger plant 7, following the coal gasifier 5 for the raw gas, a gas dust separator 8, a gas purification plant 9, a methanol synthesis plant 10 with a methanol synthesis reactor 11 and a methanol separator 12, as well as an acetic acid synthesis plant 13 with an acetic acid reactor 14, a distillation column 15 for fractionation of the liquid reaction products and a scrubbing system 16 for purification of the gaseous reaction products of the acetic acid reactor. In addition, a gas separation plant 17 is connected to the purified gas line 18 leaving the gas purification plant 9. The exhaust gas line 19 of the methanol separator 12, the exhaust gas line 20 of the scrubbing system 16 following the acetic acid reactor for the gaseous reaction products and the exhaust gas line 21 for the residual gases of the gas separation plant 17 are all connected to the combustion chamber 22 of the gas turbine power plant part 2.

The gas turbine 23 of the gas turbine power generating plant part 2 drives an air compressor 24 for the combustion air as well as a generator 25. The waste heat boiler 27 is connected to the exhaust gas line 26 of the gas turbine. The steam turbine 29 of the steam power generating station part 3 is connected to the steam line 28 of the waste heat boiler 28. In the embodiment example, the steam turbine 29 consists of a high-pressure part 30 and a low pressure part 31. The steam turbine 29 is coupled to a generator 32. The low pressure part 31 of the steam turbine 29 is followed by a condensor 33, a condensate pump 34, a feedwater tank 35 and various feedwater pumps 36, 37.

Milled coal, oxygen from the preceding air separation plant 6 as well as process steam are fed to the coal gasifier 5. The hot raw gas generated in the coal gasifier 5 first gives off its heat in the heat exchanger plant 7. The raw gas from the gasifier is a mixture of constituents including $CO_2$, CO, $H_2$, $H_2S$ and dust. The heat generates steam which is fed as live steam to the steam power generating plant part 3. Dust particles are separated from the raw gas in the dust separator 8 connected to the heat exchanger plant 7. Carbon dioxide and hydrogen sulfide are thereafter separated from the raw gas in the gas purifier 9. The purified gas containing CO and $H_2$ leaving the gas purifier 9 is fed via the purified gas line 18 to the methanol synthesis plant 10 as well as to the gas separation plant 17. In the methanol synthesis reactor 11, the purified gas is in part converted into methanol by reaction of $2H_2+CO$ $CH_3OH$. The reaction is incomplete for the reason that the ratio of $H_2$ to CO in the purified gas is in the range of 0.5 to 1 instead of at the stoichiometric ratio of 2. In order to bring the composition of the purified gas fed to the methanol synthesis reactor closer to the stoichiometric ratio desired for the methanol synthesis reaction, a gas separation plant 17 is connected to the purified gas line 18 leaving the gas purifier 9 to separate hydrogen or a fraction rich in hydrogen from the purified gas. The hydrogen separated in the gas separation plant 17 is admixed via a return line 38 to the purified gas 18, which flows into the methanol synthesis reactor 11.

This increases the hydrogen content of the purified gas entering the methanol synthesis reactor. This, in turn, has the result that a larger percentage of the purified gas/hydrogen mixture directed to the methanol synthesis plant 10 can be converted into methanol. The exact composition of the gas mixture fed to the methanol synthesis reactor can be controlled via the control valve in the purified gas line 18 leading to the methanol synthesis reactor 11 and the control valve in the line leading from line 18 to gas separaton plant 17. At times of low load, if little electric energy is taken off the power generating station 1, additional hydrogen and oxygen can be produced by connecting-up water electrolysis cells 39. The oxygen can be fed to the coal gasifier 5, as shown by the line leading from water electrolysis cells 39 to coal gasifier 5. The hydrogen from electrolysis can be admixed to the purified gas in line 18 prior to entrance into reactor 11 to obtain an approximation of the stoichiometric ratio desired for the methanol synthesis.

A part of the methanol separated in the methanol separator 12 is fed together with part of the exhaust gases of the methanol synthesis to the acetic acid reactor 14. To convert the previously generated methanol into acetic acid, only relatively little carbon monoxide need be fed in addition to any carbon monoxide which is contained in the exhaust gas of the methanol separator. Even to produce as much acetic acid as possible, only a relatively small part of the purified gas from the gas separation plant 17 is sufficient. The additional quantity of carbon monoxide gas which is required in the acetic acid synthesis is separated in the gas separation plant. This carbon monoxide gas is fed to the acetic acid reactor 14 through line 40. If a larger part of the purified gas is conducted from the purified gas line 18 via the gas separation plant 17, then more hydrogen gas can be fed to the methanol synthesis plant 10 and also more methanol can be produced. The amount of carbon monoxide gas available from the separation, which is not consumed in the conversion of at least part of the methanol into acetic acid, can be fed via the exhaust gas line 19 to the combustion chamber 22 of the gas turbine 23. In this manner, the share of purified gas to the ratio of electric power to the production of chemical raw materials can be matched within certain limits to the instantaneous requirement situation.

The acetic acid is separated from the remaining liquid reaction products in the distillation column 15. The gaseous reaction products are processed in the washing system 16 to effect separation of unconverted methanol from the gaseous components. Unconverted methanol is returned into the acetic acid reactor 14. The exhaust gases of the washing system are fed together with the exhaust gases of the methanol synthesis plant 10 and the residual gas from the gas separation plant 17, to the burner 22 of the gas turbine 23. There, they are burned together with the air supplied by the compressor 24. Burning the exhaust gases in the gas turbine minimizes or eliminates the use of purified gas for burning thereby realizing a saving either directly or by the conversion used in the production of methanol and acetic acid. Also no liquid residues which are difficult to utilize are collected.

The hot exhaust gases of the gas turbine 23 are conducted via the exhaust gas line 26 into the exhaust heat boiler 27. There, waste heat in the hot exhaust gases is used for generating steam. The steam generated in the waste heat boiler 27 as well as additional steam generated in the heat exchanger plant 7 are fed to the steam turbine 29. The process steam which is required as gasification steam and as heating steam for individual steps of the production process, is taken from the steam turbine at the appropriate pressure stages.

Figure 2:
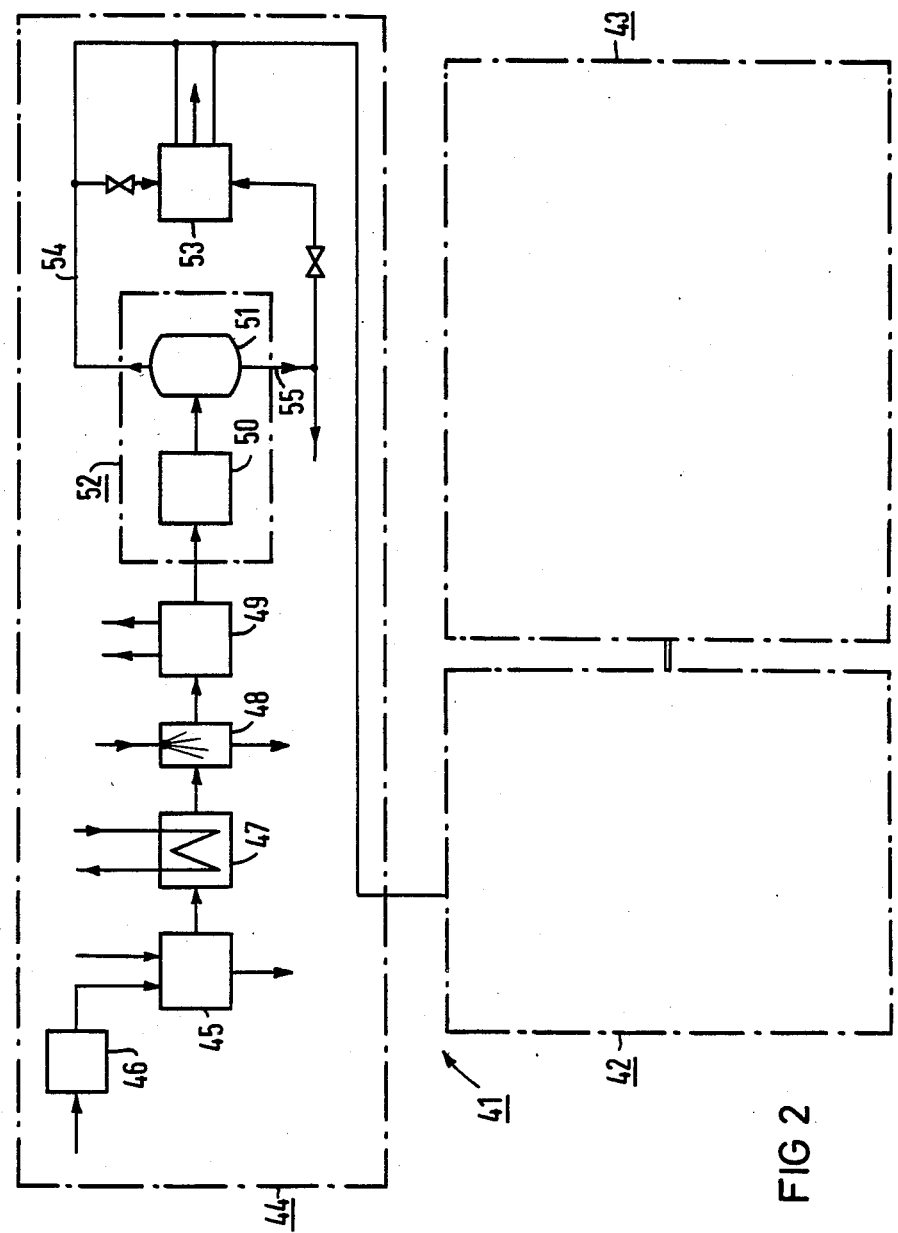
FIG. 2 shows another power generating station according to the invention with a connected plant for the manufacture of methanol and vinyl acetate.

FIG. 2 shows another power generating station 41, of which the gas turbine power generating station part 42 and the steam power generating plant part 43 are identical with those of the embodiment example of FIG. 1. The plant 44, preceding the gas turbine power generating station part for producing chemical raw materials, however, deviates from that of the embodiment example of FIG. 1. Here also, the coal gasifier 45 is associated with an air separation plant 46 and the raw gases are fed successively to a heat exchanger plant 47, a gas dust separator 48 and a gas purification plant 49. The purified gas flowing from the gas purification plant is fed to a continuous flow methanol synthesis plant 52 which consists of a methanol synthesis reactor 50 and a methanol separator 51. The methanol synthesis plant 52, however, is followed by a plant 53 for generating vinyl acetate. Their residual gases and liquid residues are fed to the gas turbine power generating plant part 42 for combustion.

In FIG. 2, as is FIG. 1, raw gas is generated in the coal gasifier 45 through reaction of milled coal with oxygen and process steam. The heat of the latter is utilized in the heat exchanger plant 47 for generating steam which can be used, as desired, as process steam or as feed steam for the steam generating plant part 43. In the gas dust separator 48, the raw gas is freed to dust particles and, at the same time, enriched with steam. In the gas purification plant 49, hydrogen sulfide gas and carbon dioxide are removed. The remaining purified gas which contains substantially hydrogen and carbon monoxide, is fed here with unchanged composition to the continuous flow methanol synthesising plant 52. Because the ratio $H_2$ to CO is in the range of 0.5 to 1, i.e. is still far removed from the stoichiometric ratio of 2, the conversion to methanol is substantially smaller than it would be if the purified gas had the desired stoichiometric composition. In the following methanol separator 51, the methanol is separated from the exhaust gas of the methanol synthesis. The exhaust line 54 and the methanol output line 55 of the methanol separator 51 are connected to the plant 53 for producing vinyl acetate.

It is of benefit if in a plant for generating vinyl acetate connected to a methanol synthesis plant 52 fed with purified gas from a coal gasifier, the overall stoichiometric ratio of $H_2$ to CO for the production of vinyl acetate via methanol from a starting gas containing $H_2$ and CO is 0.5. Such a starting gas is similar to the composition of the purified gas. This makes unnecessry a gas separation plant for enriching the purified gas with hydrogen as in the acetic acid synthesis. The excess methanol is available as a salable chemical raw material. The residual gases and liquid residues of the plant 53 for the manufacture of vinyl acetate as well as the unused portions of the synthesis exhaust gas from the methanol separator 51 can be fed to the gas turbine power generating plant part 42 and can be burned there. Their chemically bound energy is therefore not lost. Because of the possibility of burning the synthesis exhaust gas, the cost for the gas purification can be reduced as compared to known manufacturing processes because there, also the raw gas stream branched off for the vinyl acetate production must be purified to completely remove carbon dioxide and hydrogen sulfide. The vinyl acetate can therefore also be produced more inexpensively and can be sold, like the methanol, as a chemical raw material.

With this power generating plant in accordance with the invention, it is possible to match the ratio of electric energy produced and vinyl acetate by changing the amount of gas fed to the vinyl acetate synthesis, within certain limits, to the instantaneous demand situation.

The foregoing is a description corresponding, in substance, to German application P 33 20 227.3, dated June 3, 1983, international priority of which is being claimed for the instant application, and which is hereby made part of this application. Any material discrepancies between the foregoing specification and the specification of the aforementioned corresponding German application are to be resolved in favor of the latter.

We claim

1. Power generating station with an integrated coal gasification plant comprising
   (a) a coal gasification plant which contains a gasifier for gasification of coal to produce raw fuel gas containing a mixture of gaseous constituents including CO, $H_2$, $CO_2$ and $H_2S$, an air separation unit to separate air into oxygen and nitrogen, and a compressor to supply the air separation unit with air,
   (b) a gas turbine power plant which includes a gas turbine, a combustion chamber of the gas turbine, an air compressor for introduction of air into the combustion chamber, and a generator coupled to the turbine,
   (c) a steam generating station which includes a steam generator connected to an exhaust gas line of the gas turbine, a high pressure and low pressure steam turbine, a feedwater tank to collect the condensate and a feedwater pump to feed water to the steam generator,
   (d) a heat exchanger in which the raw gas is utilized to generate steam and conduit means for passage of the generated steam to the steam turbine, and a gas purification plant for the removal of impurities to produce a purified gas,
   (e) a methanol synthesis plant having a methanol synthesis reactor for the partial conversion of the purified gas from the gasifier into methanol and a methanol separator connected to the synthesis reactor for the separation of the reaction products from the synthesis reactor into liquid methanol and methanol synthesis exhaust gas,
   (f) an additional vinyl acetate synthesis plant for the utilization of at least part of the methanol and the methanol synthesis exhaust gas to produce vinyl acetate and a residual gas as a byproduct, and connecting means for supplying excess methanol synthesis exhaust gas and residual gas to the combustion chamber, including a water electrolysis plant wherein water is dissociated into oxygen and hydrogen, an oxygen line connected from the electrolysis plant to the coal gasifier and a hydrogen line to a gas feedline leading to the methanol synthesis reactor.

2. Power generating station with an integrated coal gasification plant comprising
   (a) a coal gasification plant which contains a gasifier for gasification of coal to produce raw fuel gas containing a mixture of gaseous constituents including CO, $H_2$, $CO_2$ and $H_2S$, an air separation unit to separate air into oxygen and nitrogen, and a compressor to supply the air separation unit with air,
   (b) a gas turbine power plant which includes gas turbine, a combustion chamber of the gas turbine, an air compressor for introduction of air into the combustion chamber, and a generator coupled to the turbine,
   (c) a steam generating station which includes a steam generator connected to an exhaust gas line of the gas turbine, a high pressure and low pressure steam turbine, a feedwater tank to collect the condensate and a feedwater pump to feed water to the steam generator,
   (d) a heat exchanger in which the raw gas is utilized to generate steam and conduit means for passage of the generated steam to the steam turbine, and a gas purification plant for the removal of impurities to produce a purified gas,
   (e) a methanol synthesis plant having a methanol synthesis reactor for the partial conversion of the purified gas from the gasifier into methanol and a methanol separator connected to the synthesis reactor for the separation of the reaction products from the synthesis reactor into liquid methanol and methanol synthesis exhaust gas,
   (f) an additional vinyl acetate synthesis plant containing a vinyl acetate reactor for the utilization of at least part of the methanol and the methanol synthesis exhaust gas to produce vinyl acetate and a residual gas as a byproduct, and connecting means for supplying excess methanol synthesis exhaust gas and residual gas to the combustion chamber, and
   (g) a gas separation plant is connected to a gas feedline to the methanol synthesis reactor said gas separation plant adapted to separate a fraction rich in hydrogen and a fraction rich in carbon monoxide from gas from the feedline, connecting means for admixing the hydrogen-enriched fraction to the gas stream flowing through the feedline into the methanol synthesis reactor, and connecting means for feeding the carbon monoxide-enriched fraction to the vinyl acetate reactor as well as to the combustion chamber of the gas turbine power generating plant.

3. Power generating station according to claim 1, wherein the methanol synthesis plant is without a recirculation line and loop compressor for recirculating methanol synthesis exhaust gas.

4. Power generating station according to claim 1, including connecting means to feed the exhaust gases from the plant for producing vinyl acetate together with the excess synthesis exhaust gas of the methanol synthesis plant to the combustion chamber of the gas turbine power generating plant.

5. Power generating station according to claim 1, wherein the methanol synthesis plant and the additional synthesis plant are adapted to utilize, at least partially, heat liberated in the methanol synthesis plant and in the additional synthesis plant for the generation of steam.

6. Power generating station according to claim 2, wherein the methanol synthesis plant is without a recirculation line and loop compressor for recirculating methanol synthesis exhaust gas.

7. Power generating station according to claim 2, including connecting means to feed the exhaust gases from the plant for producing vinyl acetate together with the excess synthesis exhaust gas of the methanol synthesis plant to the combustion chamber of the gas turbine power generating plant.

8. Power generating station according to claim 2, wherein the methanol synthesis plant and the additional synthesis plant are adapted to utilize, at least partially, heat liberated in the methanol synthesis plant and in the additional synthesis plant for the generation of steam.

9. Power generating station according to claim 4, including connecting means for distributing steam generated in the heat exchanger and gas purification plant together with the steam generated in the steam generator to the steam turbine of the steam power generating station part and as process steam for the chemical production of methanol and vinyl acetate.

* * * * *